United States Patent [19]

Liao et al.

[11] Patent Number: 5,188,903
[45] Date of Patent: Feb. 23, 1993

[54] SILOXANE-CONTAINING GLYCIDYL ESTERS, CURABLE COMPOSITIONS AND CURED PRODUCTS

[75] Inventors: Zeng K. Liao; James L. Bertram, both of Lake Jackson, Tex.

[73] Assignee: The Dow Chemical Company, Midland, Mich.

[21] Appl. No.: 737,627

[22] Filed: Jul. 30, 1991

[51] Int. Cl.$^5$ ................................................. B32B 9/04
[52] U.S. Cl. ..................................... 428/447; 528/15; 528/26; 528/31
[58] Field of Search ............................. 528/15, 26, 31; 428/447

[56] References Cited

U.S. PATENT DOCUMENTS

| | | |
|---|---|---|
| 3,787,452 | 1/1974 | Leumann et al. ............... 260/348 |
| 3,867,322 | 2/1975 | Leumann et al. ............... 260/18 |
| 3,926,885 | 12/1975 | Keil .................................. 260/29.6 |
| 3,996,195 | 12/1976 | Sato et al. ....................... 528/15 |
| 4,276,252 | 6/1981 | Kreis et al. ...................... 264/222 |
| 4,283,513 | 5/1981 | Mikami ............................ 525/476 |
| 4,398,010 | 8/1983 | Adkins ............................. 528/15 |
| 4,588,800 | 5/1986 | Palensky et al. ................ 528/15 |
| 4,604,435 | 8/1986 | Koshii et al. .................... 525/476 |
| 4,707,529 | 11/1987 | Hoffman et al. ................. 525/476 |
| 4,906,677 | 3/1990 | Barsotti et al. .................. 523/400 |
| 4,954,580 | 9/1990 | Zahir ............................... 525/476 |

FOREIGN PATENT DOCUMENTS 0263237 5/1987 European Pat. Off. .

OTHER PUBLICATIONS

"Siloxane Modifiers for Epoxy Resins", Chapter 10, *Advances in Chemistry Series 208 Rubber Modified Thermoset Resins, American Chemical Society*, 1984.
"Rubber-Modified, Flame-Retardant, High Glass Transition Temperature Epoxy Resins", Chapter 17, *Advances in Chemistry Series 208 Rubber Modified Thermoset Resins, American Chemical Society*, 1984.
"Impact Properties of Rubber-Modified Epoxy Resin-Graphite-Fiber Composites", Chapter 20.
*Advances in Chemistry Series 208 Rubber Modified Thermoset Resins, American Chemical Society*, 1984.

*Primary Examiner*—Melvyn I. Marquis

[57] ABSTRACT

Glycidyl esters containing at least one glycidyl ester group and at least one organo siloxane moiety per molecule are prepared by reacting (1) at least one compound containing at least one glycidyl ester group per molecule and at least one unsaturated aliphatic or cycloaliphatic group per molecule; with (2) a compound containing at least one hydrosiloxane moiety per molecule.

10 Claims, No Drawings

SILOXANE-CONTAINING GLYCIDYL ESTERS, CURABLE COMPOSITIONS AND CURED PRODUCTS

FIELD OF THE INVENTION

The present invention pertains to glycidyl ester compounds containing at least one siloxane moiety. curable compositions thereof and cured products.

BACKGROUND OF THE INVENTION

Diglycidyl esters of cycloaliphatic diacids are commercially available such as (a) the diglycidyl ester prepared from cis-1,2,3,6-tetrahydrophthalic annydride commercially available from Ciba-Geigy as Araldite TM CY192 and (b) the diglycidyl ester of cis-1,2-cyclohexanedicarboxylic acid commercially available from Bayer as Lekutherm TM X100 and Ciba-Beigy as Araldite TM CY184. These diglycidyl esters of cycloaliphatic diacids are useful in casting and molding of electronic and electrical components for outdoor applications.

Glycidyl esters of cycloaliphatic carboxylic acids are very reactive with anhydride curing agents. U.S. Pat. No. 4,906,677 discloses multi-component coating compositions comprising an anhydride containing polymer, a glycidyl component and a phosphonium catalyst.

There are few polyglycidyl esters commercially available except for copolymers of glycidyl methacrylate esters and styrene and other acrylic esters. However, these copolymers are solid and need high levels of sovent(s) for processing.

It would be desirable to have available multi-functional glycidyl esters which are easily prepared and have a low viscosity.

It would also be desirable to have available glycidyl ester compounds which exhibit an improvement in one or more of the properties such as increased pot life when formulated with a curing agent, or when cured, an improvement in one or more of the properties such as moisture resistance, weatherability, or flexibility.

The property improvement is observed when compared to like compositions which are free of any siloxane moieties.

SUMMARY OF THE INVENTION

One aspect of the present invention concerns compounds containing at least one glycidyl ester group and at least one organosiloxane moiety

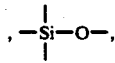

per molecule: with the proviso that said compound containing at least one glycidyl ester group and at least one organosiloxane moiety per molecule contains at least one silicon atom linked to a carbon atom contained in the portion of the molecule which contains a glycidyl ester group.

Another aspect of the present invention concerns to a process for preparing compounds containing at least one glycidyl ester group and at least one organosiloxane moiety per molecule.

A further aspect of the present invention concerns compositions comprising (A) at least one compound containing at least one glycidyl ester group and at least one organosiloxane moiety per molecule; and (B) a curing quantity of at least one curing agent for component (A).

A still further aspect of the present invention concerns the product or article resulting from curing the aforementioned curable compositions.

A further aspect of the present invention concerns a coating composition comprising the aforementioned curable compositions.

The glycidyl ester compounds of the present invention exhibit an improvement in one or more of the properties such as increased pot life when formulated with a curing agent, or when cured, an improvement in one or more of the properties such as moisture resistance, stain resistance, weatherability, or flexibility. Improvements in other mechanical, chemical or thermal properties may also be observed.

The property improvement is observed when compared to like compositions which are free of any siloxane moieties.

The present invention may suitably comprise, consist of, or consist essentially of, the aforementioned components and compounds.

The invention illustratively disclosed herein suitably may be practiced in the absence of any component which is not specifically disclosed or enumerated herein and any of the compounds may contain or be free of any substituent not specifically named herein.

DETAILED DESCRIPTION OF THE INVENTION

The compounds of the present invention containing at least one glycidyl ester group and at least one organosiloxane moiety per molecule are prepared by reacting (1) at least one compound containing at least one glycidyl ester group per molecule and at least one unsaturated aliphatic or unsaturated cycloaliphatic group per molecule with (2) a compound containing at least one hydrosiloxane moiety per molecule.

The product resulting from the reaction of component (1) with component (2) is through the hydrogen atom attached to the silicon atom of component (2) and unsaturated aliphatic or unsaturated cycloaliphatic group of component (1), resulting in a direct bond between the silicon atom and a carbon atom containing the double bond before the double bond's disappearance by reaction with the hydrosiloxane moiety.

The reaction is usually conducted at temperatures of from about 0° C. to about 150° C., preferably from about 30° C. to about 120° C., more preferably from about 40° C. to about 100° C. for a time sufficient to complete the reaction, usually from about 0.5 to about 15, preferably from about 1 to about 10, more preferably from about 2 to about 6 hours.

At temperatures below about 0° C., the reaction is very slow.

At temperatures above about 150° C., a severely exothermic reaction occurs. Such a reaction is very difficult to control and is undesirable.

The reactants are employed in amounts which provide an equivalent ratio of hydrosiloxane groups to unsaturated glycidyl ester-containing compound of from about 0.25:1 to about 25:1, preferably from about 0.5:1 to about 10:1, more preferably from about 0.75:1 to about 5:1.

The reaction is usually and preferably conducted in the presence of a homogeneous catalyst such as, for example, chloroplatinic acid (H$_2$PtCl$_6$), as well as ((C$_2$H$_4$)PtCl$_2$)$_2$, bis-(triphenylphosphine)cobalt chloroiridium (IrClCo(PPh$_3$)$_2$), dicobalt octacarbonyl (Co$_2$(CO)$_8$). Also, 10% Pd/C or 5% Pt/C and Raney Ni are effective catalysts for this reaction. Hydrosilylation catalysts which can be used also include those disclosed in U.S. Pat. Nos. 3,775,442, 3,159,601, 3,220,972, all of which are incorporated herein by reference. An effective amount of a platinum catalyst is from about 0.0005 to 1.05 percent by weight of platinum based on the weight of the hydrosilylation mixture.

Also, if desired, the reaction can be conducted in the presence of a solvent such as, for example, aliphatic, cycloaliphatic or aromatic hydrocarbons, or any combination thereof. Particularly suitable solvents include, for example, n-hexane, cyclohexane, octane, methylene chloride, chloroform, chlorobenzene, toluene, xylene, any combination thereof and the like.

The excessive unreacted ≡Si—H bonds are terminated, quenched, by addition of a mono- or di-unsaturated aliphatic or cycloaliphatic alkene having from about 4 to about 20, preferably from about 6 to about 16, more preferably from about 7 to about 12, carbon atoms or an aromatic compound substituted with an unsaturated aliphatic or cycloaliphatic alkene group having from 8 to about 20 carbon atoms, such as, for example, styrene, α-methyl styrene, noborylene, n-octene, cyclohexene, dicyclopentadiene, and the like. This is accomplished by reaction at a temperature of from about 0° C. to about 150° C., preferably from about 30° C. to about 120° C., more preferably from about 40° C. to about 100° C. for a time sufficient to complete the reaction, usually from about 0.5 to about 15, preferably from about 1 to about 10, more preferably from about 2 to about 6 hours. Likewise, this reaction is conducted in the presence of the aforementioned heterogeneous catalysts, and can also, if desired, be conducted in the presence of the aforementioned solvents.

At temperatures below about 0° C., excess unreacted ≡Si-H bonds cannot be fully terminated.

At temperatures above about 150° C., a severely exothermic reaction occurs. Such a reaction is very difficult to control and is undesirable.

This hydrosilylation method is describe by John L. Speier in Advances in Organometallic Chemistry, vol. 17, Academic Press, Inc., pp 407–447, 1979 which is incorporated herein by reference in its entirety.

Suitable organosiloxane compounds which can be employed include, for example, those represented by the following general formulas I, II, III or IV Formula I

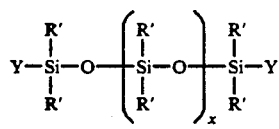

Formula II

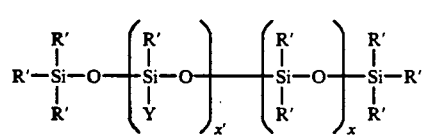

Formula III

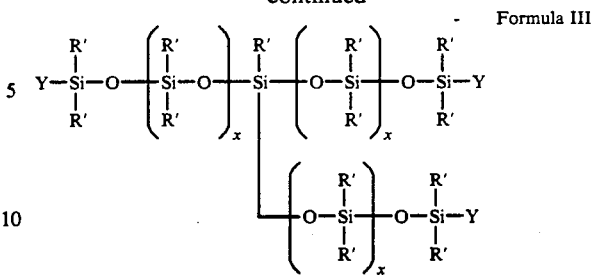

Formula IV

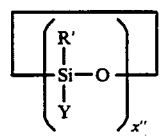

wherein each R' is independently a hydrocarbyl group or hydrocarbyl group substituted with N or F containing groups, said hydrocarbyl group having from 1 to about 20, preferably from 1 to about 10, more preferably from 1 to about 4, carbon atoms; each Y is hydrogen; each x independently has a value from zero to about 500, preferably from zero to about 250, more preferably from zero to about 125; each x' independently has a value from 2 to about 500, preferably from 2 to about 250, more preferably from 2 to about 125; x" has a value from 3 to about 50, preferably from about 3 to about 10, more preferably from about 3 to about 5; and the sum of x and x' is from about 2 to about 1000, preferably from about 2 to about 500, more preferably from about 2 to about 250.

Particularly suitable organohydrosiloxane compounds which can be employed include, for example, 1,1,3,3-tetramethyldisiloxane; 1,1,3.3,5,5-hexamethyltrisiloxane; 1,1,3,3,′5′,5,7,7-octamethyltetrasiloxane; 1,3-diphenyl-1,3-dimethyldisiloxane; 1,1,3,3-tetraisopropyldisiloxane: 1,3-diphenyl-1,1′,3,3-tetrakis-(dimethylsiloxyl)disiloxane;; 1,1,3,3-tetrakis-(trimethylsiloxyl)disiloxane; methyl hydrocyclosiloxane {(CH$_4$OSi)n where n=4–20} such as 1,3,5,7-tetramethylhydrocyclotetrasiloxane, 1,3,5,7,9-pentamethylhydrocyclopentasiloxane, 1,3.5,7,9,11-hexamethylhydrocyclohexasiloxane, polymethylhydrosiloxane (weight average M.W.=300 to 50,000): methylhydro-dimethylsilyoxane copolymer (weight average M.W.=120 to 100,000): dimethylterminated-methylhydro-phenylmethylsiloxane copolymer (weight average M.W.=120 to 100,000): any combination thereof and the like.

Also included as suitable organosiloxane compounds having a terminal hydrosiloxyl structure are, for example, those represented by the general formulas HSi(CH$_3$)$_2$—O—(Si(CH$_3$)$_2$)$_n$—O—Si(CH$_3$.)$_2$—R—Si(CH$_3$)$_2$—O—(Si(CH$_3$)$_2$)$_n$—Si(CH$_3$)$_2$H, or

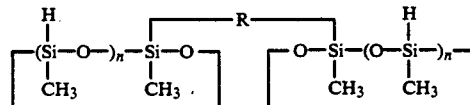

wherein R is a divalent saturated aliphatic or divalent saturated cycloaliphatic group having from about 4 to about 100, preferably from about 4 to about 50, more preferably from about 4 to about 20 carbon atoms.

Suitable glycidyl ester compounds containing unsaturated aliphatic or unsaturated cycloaliphatic groups which can be employed herein include, those represented by the general formula $$(R^3-OOC)_n-R^2-(COO-R^1)_m$$

wherein $R^1$ is an saturated or unsaturated aliphatic, saturated or unsaturated cycloaliphatic, aromatic. or sulfur, nitrogen or phosphorus containing heterocyclic saturated or unsaturated cycloaliphatic or aromatic group; $R^2$ is a saturated or unsaturated aliphatic or saturated or unsaturated cycloaliphatic, or sulfur, nitrogen or phosphorus containing heterocyclic saturated or unsaturated cycloaliphatic group: $R_3$ is a glycidyl group or lower alkyl ($C_1$-$C_4$) substituted glycidyl group: and each n and m independently has a value from 1 to about 20, preferably from 1 to about 10, more preferably from 1 to about 5: and with the proviso that there is at least one unsaturated moiety in each molecule undergoing hydrosilylation and when $R^2$ contains an unsaturated moiety, $R^1$ can be a glycidyl group.

Particularly suitable $R^1$ groups include, for example, $-CH_2-CH=CH_2$, $-CH=CH_2$, $-(CH_2-CHR''-O)_z-CH_2-CH=CH_2$ where R" is hydrogen or $C_1-C_6$ alkyl group and z has a value from 1 to 50, bicyclo-(2.2.1)-hept-1-enyl, styrenyl, vinylbenzyl, any combination thereof and the like.

It is preferred that the glycidyl ester compounds containing unsaturated aliphatic or unsaturated cycloaliphatic groups contain an average of no more than two such unsaturated groups so as to prevent gellation during the silylation reaction in some instances.

The glycidyl ester compounds containing unsaturated aliphatic or unsaturated cycloaliphatic groups which can be employed herein can be prepared by reacting an aliphatic, cycloaliphatic or aromatic dicarboxylic acid, polycarboxylic acid or anhydride or polyanhydride thereof with an unsaturated aliphatic, unsaturated cycloaliphatic or aromatic compound containing an aliphatic hydroxyl group.

Suitable aliphatic, cycloaliphatic or aromatic dicarboxylic acids, polycarboxylic acids or anhydrides or polyanhydrides thereof which can be employed to prepared the glycidyl ester compounds containing unsaturated aliphatic or unsaturated cycloaliphatic groups usually have from about 2 to about 50, preferably from about 4 to about 30, more preferably from about 6 to about 15, carbon atoms per molecule. Particularly suitable acids or anhydrides include, for example, oxalic acid, phthalic acid, maleic acid, succinic anhydride, citraconic anhydride, itaconic anhydride, dodecenyl succinic anhydride, phthalic anhydride, hexahyhdrophthalic anhydride, tetrahydrophthalic anhydride, trimellitic anhydride, 1,2-cyclobutane dicarboxylic anhydride, bicyclo2.2.1heptene-2,3-dicarboxyilic anydride isomers (Nadic Anydride), methylbicyclo[2.2.1]heptene-2,3-dicarboxyilic anydride isomers (Nadic Methyl Anydride), any combination thereof or the like.

Suitable unsaturated aliphatic, unsaturated cycloaliphatic or aromatic compound containing an aliphatic hydroxyl group include those represented by the formula $$R^1-(OH)_m$$

wherein $R^1$ is a defined above and m has a value from 1 to about 4, preferably from 1 to about 3, more preferably from 1 to about 2.

Particularly suitable unsaturated aliphatic, unsaturated cycloaliphatic or aromatic compound containing an aliphatic hydroxyl group include, for example, allyl alcohol, crotyl alcohol, 3-buten-1-ol, 3-buten-2-ol, norbornene methanol, or any combination of any two or more such unsaturated aliphatic, unsaturated cycloaliphatic or aromatic compounds containing an aliphatic hydroxyl group.

The reactants are employed in amounts which provide a molar ratio of acid- or anhydride-containing compound to hydroxyl-containing compound of from about 0.6:1 to about 1.5:1, preferably from about 0.8:1 to about 1.3:1, more preferably from about 0.9:1 to about 1.2:1.

The reaction is conducted at a temperature of from about 10° C. to about 200° C., preferably from about 30° C. to about 150° C., more preferably from about 40° C. to about 100° C. for a time sufficient to complete the reaction, usually from about 0.5 to about 8. preferably from about 1 to about 6, more preferably from about 2 to about 4 hours.

At temperatures below about 10° C., the reaction is very slow and usually results in an incomplete reaction of the reactants.

At temperatures above about 200° C., the unsaturated compounds become unstable.

If desired, the reaction can be conducted in the presence of a suitable inorganic or organic acid catalyst, such as, for example, HCl, $H_2SO_4$, $BF_3$.etherate, $TiCl_4$, $ZrCl_4$, p-toluene sulfonic acid, methane sulfonic acid, trifluromethane sulfonic acid, any combination therof, or any combination thereof and the like. When employed, these catalysts are employed in amounts of from about 0.01 to about 5, preferably from about 0.5 to about 2 percent by weight based upon the weight of the reactants.

Also, the reaction can be conducted in the presence of the aforementioned solvents.

The resultant unsaturated ester-acid compound is then reacted, in the presence of a suitable catalyst, with at least a molar excess of an epihalohydrin or a $C_1$-$C_4$ alkyl substituted epihalohydrin, such as, for example epichlorohydrin, epibromohydrin, epiiodohydrin, methylepichlorohydrin, methylepibromohydrin, methylepiiodohydrin, or any combination thereof and the like.

The reaction is usually conducted at temperatures of from about 10° C. to about 90° C., preferably from about 20° C. to about 80° C., more preferably from about 30° C. to about 70° C. for a time sufficient to complete the reaction, usually from about 0.5 to about 8, preferably from about 1 to about 6. more preferably from about 2 to about 4 hours.

At temperatures below about 10° C., an incomplete reaction results.

At temperatures above about 200° C., side reactions occur which reduces the epoxide content of the unsaturated glycidyl ester compound.

If desired, the reaction can be conducted in the presence of a suitable ammonium, phosphonium or phosphine catalyst, such as, for example, benzyl trimethyl ammonium chloride, benzyl trimethyl ammonium bromide, ethyltriphenylphosphonium chloride, ethyltriphenylphosphonium bromide, tetramethyl ammonium bromide, ethyltriphenylphosphonium iodide, tetrabutyl ammonium chloride, tetrabutyl ammonium bromide, tetrabutyl ammonium iodide, ethyltriphenylphosphonium acetate.acetic acid complex, tetrabutyl phosphonium acetate.acetic acid complex, triehtylphosphine, tripropylphosphine, triphenylphosphine, tetramethyl ammonium hydroxide, or any combination thereof and the like.

The epihalohydrin and the compound having groups reactive with a vicinal epoxide group are employed in amounts which provide a ratio of moles of epihalohydrin per group reactive with an epoxide group from 1:1 to 15:1, preferably from 1.5:1 to 12:1, more preferably from 1.5:1 to 10:1.

At ratios below 1:1, complete reaction of the reactive group with the epihalohydrin cannot be achieved.

At ratios above 15:1, the productivity (capacity) of the reactor is reduced.

After the coupling reaction is essentially complete, the epoxidation reaction is carried out by the addition of alkali or alkaline earth metal hydroxide solutions.

Suitable alkali or alkaline earth metal hydroxides which can be employed herein include, for example, sodium hydroxide potassium hydroxide lithium hydroxide, barium hydroxide, calcium hydroxide, magnesium hydroxide, or any combination thereof and the like. Also suitably used in the present invention is manganese hydroxide either alone or in combination with the alkali or alkaline earth metal hydroxide.

The alkali or alkaline earth metal hydroxide is employed in an amount which provides a ratio of hydroxide groups to carboxyl group of from 0.8:1 to about 1.2:1.

The alkali or alkaline earth metal hydroxide can be employed in solution with water or an organic solvent such as alcohols, sulfoxides or amides; for example, methanol, ethanol, isopropanol, dimethylsulfoxide, dimethylacetamide, or any combination thereof and the like. Water is the preferred solvent for the alkali or alkaline earth metal hydroxide. The alkali or alkaline earth metal hydroxide solution is employed in a concentration from about 10 to about 70, preferably from about 30 to about 50 percent alkali or alkaline earth metal hydroxide by weight.

Suitable solvents which can be employed herein include, for example, ketones, linear cyclic ethers, primary, secondary and tertiary alcohols, glycol monoethers, glycol ether acetates, aromatic or cycloaliphatic or aliphatic hydrocarbons having from 6 to 12 carbon atoms, or any combination thereof and the like. Any of the aforementioned solvents can be employed herein so long as the solvent does not react with the components of the reaction mixture. In addition, the solvent should have a boiling point such that the solvent is not totally removed from the reaction mixture during co-distillation of the water, epihalohydrin and solvents. Particularly suitable such solvents include, for example, 1-methoxy-2-hydroxy propane, 1-butoxy-2-hydroxy ethane, tert-amyl alcohol, tert-hexyl alcohol, 1-isobutoxy-2-hydroxy propane, 1-phenoxy-2-hydroxy propane, cyclohexanol, dioxane, 1,2-diethoxyethane, 2-methoxyethyl ether, ethylene glycol monomethyl ether acetate, ethyl acetate, isobutyl acetate, isoamyl acetate, methyl ethyl ketone, methyl isobutyl ketone, dimethyl sulfoxide, dimethyl acetamide, N-methylyrrolidinone, dimethyl formamide, dimethylsulfone, tetramethyil urea, hexamethyl phosphoramide, tetramethylenesulfolane, any combination thereof and the like.

The solvents are employed in amounts such that the amount of solvent in the initial epihalohydrin solvent mixture is from about 5 to about 80, preferably from about 5 to about 50, more preferably from about 10 to about 40 percent solvent based upon the combined weight of solvent plus epihalohydrin.

The process of the present invention can employ procedures for continuously removing the water produced in the reaction mixture by codistilling or azeotroping the water with epihalohydrin and solvent, if employed. The epihalohydrin and solvent, if employed, is separated from the water and returned to the reaction mixture. This method is described by Wang et al. in U.S. Pat. No. 4,499,255 and U.S. Pat. No. 4,778,863 which are incorporated herein by reference.

The siloxane-containing glycidyl esters of the present invention can be represented by the following general formulas V, VI, VII and VIII

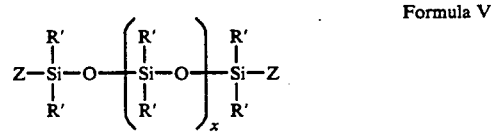

Formula V

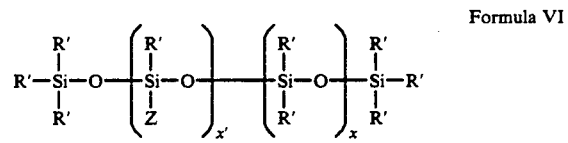

Formula VI

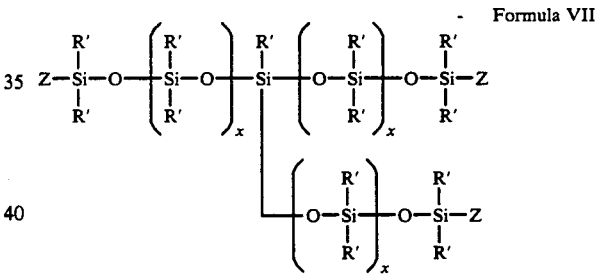

Formula VII wherein R' is independently a hydrocarbyl group or hydrocarbyl group substituted with N or F containing groups, said hydrocarbyl group having from 1 to about 20, preferably from 1 to about 10, more preferably from 1 to about 4, carbon atoms; each Z is an aliphatic or

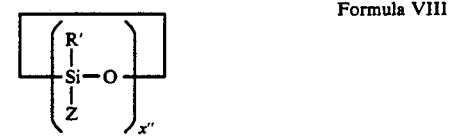

Formula VIII cycloaliphatic group containing a glycidyl ester moiety represented by the general formula —X—R$^5$—(-COOR$^4$)$_{n'}$, with the proviso that the Z group is attached directly to a silicon atom; R$^5$ is an aliphatic or cycloalilphatic or aromatic group or a S, N or P containing heterocyclic group having from 1 to about 50, preferably from 1 to about 25, more preferably from 1 to about 15 carbon atoms; R$^4$ is a glycidyl group or lower alkyl (C$_{1-4}$) substituted blycidyl group; n' has a value from 1 to about 20, preferably from 1 to about 10, more preferably from 1 to about 5; each X is independently a divalent aliphatic or a divalent cycloaliphatic group or a divalent alkoxy or a divalent cycloalkoxy group having from 2 to about 30, preferably from 2 to about 20, more preferably from zero to about 250, more preferably from zero to about 125; each x' independently has a value from 2 to about 500, preferably from 2 to about 250, more preferably from 2 to about 125; x" has a value from 3 to about 50, preferably from about 3 to about 10, more preferably from about 3 to about 5; and the sum of x and x' is from about 2 to about 1000, preferably from about 2 to about 500, more preferably from about 2 to about 250.

Of particular interest are the siloxane-containing glycidyl esters of the aforementioned formulas V–VIII wherein Z is selected from one of the following with the proviso that at least one of the Z groups within each molecule contain a glycidyl ester group:

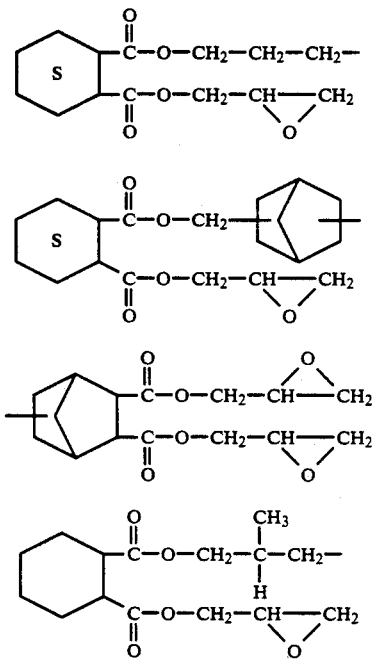

The glycidyl ester functionalized organosiloxane compounds of the present invention can be blended with any epoxy resin, or reactive epoxide diluent i.e. any compound containing an average of one or more then one vicinal epoxide group per molecule. These epoxy resins can be aliphatic, cycloaliphatic or aromatic based epoxy resins. They can be glycidyl derivatives of saturated or unsaturated aliphatic or cycloaliphatic or aromatic compounds having an average of more than one active hydrogen atom reactive with an epoxide group. Such epoxy resins are usually prepared by reacting the active hydrogen-containing compound such as an acid, hydroxyl-containing compound or an amine with an epihalohydrin such as epichlorohydrin and subsequently or simultaneously dehydrohalogenating the resultant halohydrin intermediate with a basic acting compound such as an alkali metal hydroxide. Particularly suitable such epoxy resins include, for example, the glycidyl ethers of alkylene glycols, polyalkylene glycols, polyhydric phenols, biphenols, phenol- or substituted phenol-aldehyde novolak resins, trisphenol methine, any combination thereof and the like. Also suitable are the glycidyl esters of aliphatic, cycloaliphatic or aromatic carboxylic acids having an average of more than one carboxylic acid group per molecule, such as, for example, the diglycidyl esters of cis-1,2-cyclohexanedicarboxylic acid anhydride. Also suitable are the copolymers of glycidyl esters of methacrylic or acrylic acid polymerized with other acrylic esters, styrene, vinyl toluene, α-methyl styrene, or any combination thereof or the like. The weight average molecular weight of these copolymers are usually in the range of from about 200 to about 200,000, preferably from about 500 to about 100,000, more preferably from about 1,000 to about 50,000. Also suitable are the cycloaliphatic or aliphatic epoxides prepared by the peroxidation of unsaturated double bonds.

Any suitable curing agent for epoxy resins can be employed herein to cure the glycidyl ester compounds of the present invention including, for example, primary and secondary polyamines. carboxylic acids and anhydrides thereof, phenolic hydroxyl-containing compounds, guanidines, biguanides, urea-aldehyde resins, melamine-aldehyde resins, alkoxylated urea-aldehyde resins, alkoxylated melamine-aldehyde resins, or any combination thereof or the like.

Particularly suitable curing agents include, for example, oxalic acid, phthalic acid, maleic acid, succinic anhydride, citraconic anhydride, itaconic anhydride, dodecenyl succinic anhydride, phthalic anhydride, hexahydrophthalic anhydride, tetrahydrophthalic anhydride, trimellitic anhydride, 1,2-cyclobutanedicarboxyic anhydride, benzophenonetetracarboxylic anhydride, pyromellitic anhydride, Nadic TM anhydride, methylNadic TM anhydride, or any combination thereof or the like. Also suitable are the anhydride derivatives of organosiloxane compounds which are disclosed by H. S. Ryang in U.S. Pat. No. 4,381,396, by H. S. Ryang in U.S. Pat. No. 4,511,701, by MK. A. Buese in U.S. Pat. No. 4,598,135, and by J. E. Hallgren et al. in U.S. Pat. No. 4,634,755, all of which are incorporated herein by reference. Particularly suitable such curing agents include, 5,5'-(1,1,3,3-tetramethyl-1,3-disiloxanediyl)bis-norbornane-2,3-dicarboxylic anhydride, dianhydride terminated polydiorganosiloxanes having a weight average molecular weight of from about 200 to about 100,000, norborenyl anhydride substituted cyclicorganosiloxane having a weight average molecular weight of from about 250 to about 50,000, or any combination thereof and the like.

Also included as suitable curing agents are the copolymers of Methyl Nadic Anhydride or maleic anhydride or maleic acid or fumaric acid with styrene, butadiene or other unsaturated monomers containing 2 to 20 carbon atoms, or any combination thereof such copolymers or the like. These copolymers are disclosed by Barsotti et al. in U.S. Pat. No. 4,906,677, which is incorporated herein by reference in its entirety. When the glycidyl ester compounds of the present invention are formulated with such curing agents, the formulated component has a longer pot life as compared to the formulated components from existing glycidyl esters. The weight average molecular weight of these copolymers range from about 100 to about 350,000, preferably from about 500 to about 200,000, more preferably form about 1,000 to about 100,000.

Also suitable curing agents include phenolic compounds such as, for example, novolac resins prepared from phenol or $C_1$–$C_{10}$ alkyl- or halogen-substituted phenols and an aldehyde. Suitable aldehydes include, for example, formaldehyde, acetaldehyde, furfuraldehyde. Suitable phenols include, phenol, cresol, bromophenol, any combination thereof and the like. Also suitable as the phenolic curing agent are the bisphenols such as, for example, biphenol, bisphenol A, bisphenol F, bisphenol K, bisphenol S, dicyclopentadienyl-bis(2,6-dimethylphenol), dicylopentadienyl-bisphenol, any combination thereof and the like.

Also suitable as curing agents include, for example, 2-dimethylilimidazole, 2-ethyl-4-methylimidazole, dicyandiamide, ethylendiamine, diethylenetriamine, triethylenetetramine, diaminocyclohexane, 4,4'-methyilenedicyclohexylamine, 1,3-phenylenediamine, sulfanilimide, aminoethylpiperazine, 4,4'-diaminodiphenylmethane, 3,3'-diaminodiphenylmethane, 4,4'-diaminodiphenylsulfone, any combination thereof and the like.

Also suitable as curing agents are the Lewis acids such as, for example, boron trifluoride or ether complexes thereof.

Suitable catalysts for the curing agents include for example, Lewis bases such as, for example 2-methyimidazole, 2-ethylimidazole, benzendedimethylamine, 2,4,6-tri(dimethylamino)-phenol, any combination thereof and the like.

Also suitable as catalysts are the latent catalysts taught by Bertram et al. in U.S. Pat. No. 4,925,901 and U.S. Pat. No. 5,946,817 which are incorporated herein by reference.

The curing agents are employed in an amount which will effectively cure the composition containing the epoxy resin. These amounts will depend upon the particular modified epoxy resin and curing agent employed however, suitable amounts include, for example, from about 0.5 to about 1.5, preferably from about 0.75 to about 1.25, more preferably from about 0.9 to about 1.1 equivalents of curing agent per epoxide equivalent for those curing agents which cure by reacting with the epoxy group of the epoxy resin or per hydroxyl group for those curing agents which cure by reacting with the aliphatic hydroxyl groups along the backbone of the epoxy resin. The *Handbook of Epoxy Resins* by Lee and Neville, McGraw-Hill, 1967 contains various discussions concerning the curing of epoxy resins as well as compilation of suitable curing agents. This handbook is incorporated herein by reference.

The glycidyl ester epoxy resins containing organosiloxane moieties of the present invention can be blended with other materials such as solvents or diluents, fillers, pigments, dyes, u. v. absorbants, flow modifiers, thickeners, reinforcing agents, any combination thereof and the like.

These additives are added in functionally equivalent amounts e.g., the u. v. absorbants, pigments and/or dyes are added in quantities which will provide the composition with the desired color; however, they are employed in amounts of from about 0.001 to about 70, preferably from about 0.01 to about 50, more preferably from about 0.1 to about 25 percent by weight based upon the weight of glycidyl ester functionalized organosiloxane.

Solvents or diluents or carriers which can be employed herein include, for example, hydrocarbons, ketones, glycol ethers, alcohols acetates, halogenate hydrocarbons, any combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, butanol, ethyl acetate, butyl acetate, 1-methoxy-2-propanol acetate, combinations thereof and the like.

The modifiers such as thickeners, flow modifiers and the like can be employed in amounts of from about 1 to about 90, preferably from about 5 to about 80, more preferably from about 10 to about 60 percent by weight based upon the weight of epoxy resin.

Reinforcing materials which can be employed herein include natural and synthetic fibers in the form of woven, mat, monofilament, multifilament, and the like. Suitable reinforcing materials include, glass, ceramics, nylon, rayon, cotton, aramid, graphite, any combination thereof and the like.

Suitable fillers which can be employed herein include, for example, inorganic oxides, ceramic microspheres, plastic microspheres, fumed silica, combinations thereof and the like.

The fillers can be employed in amounts from about 1 to about 90, preferably from about 5 to about 80, more preferably from about 10 to about 70 percent by weight based upon the weight of the epoxy resin.

The solvents, diluents or carriers are usually employed in amounts which provide the composition with a suitable or appropriate application viscosity which varies with the application method being employed. Those to whom this invention is directed are well familiar with the application viscosities and methods employed to use the compositions of the present invention.

The present invention is useful in the preparation of coatings, castings, laminates, composites, electrical and electronic encapsulants, adhesives, sealants,.and the like.

The following examples are illustrative of the invention, but are not to be construed as to limiting the scope thereof in any manner.

EXAMPLE 1

(A) Preparation of the unsaturated mono-ester acid adduct from hexahydrophthalic anhydride and allyl alcohol A 250 ml four-necked round bottom flask equipped with a cooling condenser, mechanical stirrer, thermometer with temperature controller and nitrogen source is placed on a heating mantle. Hexahydrophthalic anhydride (HHPA, 1 mole, 154.17 g, >95% purity and allyl alcohol (1.1 mole, 63.88 g, >98% purity) are charged into the flask and carefully heated to 70° C. to 75° C. A slightly exothermic reaction occurs. The melted mixture is reacted at 75° C. to 80° C. for 4–6 hours. The unreacted allyl alcohol is further stripped off from the viscous adduct of HHPA-allyl alcohol at <100° C./5 mm Hg. 194 g. of HHPA-allyl alcohol mono-ester adduct is obtained. IR shows that absorption bands at 1860 cm$^{-1}$ and 1800cm$^{-1}$ for anhydride carbonyl group are substituted by two strong absorption bands at 1700cm$^{-1}$ and 1735 cm$^{-1}$, which represents the carbonyl groups of both ester and carboxylic acid, together with a broad carboxylic acid OH absorption peak at 3000 cm$^{-1}$ to 3500 cm$^{-1}$. H NMR(CDCl$_3$-TMS) shows the appearance of unsaturated double bond of allyl alcohol at 5-6.3ppm together with the —OCH$_2$— doublet peaks at 4.4 to 4.6 ppm for allylic mono-ester. The carboxilic absorption peak of the adduct is at 10ppm which disappears later after epoxidation.

(B) Preparation of the allyl-glycidyl hexahydrophthalate.

A 500 ml four-necked, round bottom flask equipped with a cooling condenser, mechanical stirrer, thermometer with temperature controller and addition funnel is placed on a heating mantle. 85 g (0.39 mole) of the mono-ester acid adduct prepared in (A) above, epichlorohydrin (298 g, 3.12 mole), and tetramethyl ammonium hydroxide.$5H_2O$ (0.55 g, 0.002 mole) are charged into the flask. The mixture is carefully heated to 60° C. and kept at 60° C.-62° C. for another 3 hours. IR spectra of the reaction mixture shows all carboxylic groups of the mono-ester acid adduct from HHPA and allyl alcohol reacts with epichlorohydrin to form chlorohydrin ester. Seventy-five grams of t-amyl alcohol is then added to the mixture. The reaction mixture is then cooled to 50° C.-52° C. where 35.2 g (0.68 mole) of 50% NaOH aqueous solution (0.68 mole) is added at this temperature over about a period of about 4 hours at reduced pressure (85 to 100 mm Hg) with azeotropic or co-distillation of water, solvent and epihalohydrin from the mixture and subsequently returning the solvent and epichlorohydrin to the reactor. After the completion of addition, the reaction is maintained at 50° C.-52° C. for another 30 minutes. After filtering to remove the precipitated salt, to the solution (filtrate) is added 500 ml methyl ethyl ketone (MEK), followed by neutralization with dry ice, followed by washing successively with water (100 ml/each for five times). The unreacted epichlorohydrin and MEK is then stripped off under vacuum (<5 mm Hg) at 100° C. to 130° C. 95 g. of glycidyl ester of HHPA-allyl alcohol adduct is obtained having an epoxide content of 15.39% (EEW=279). Theoretical epoxide content is 16.03% (EEW=268.2).

(C) Preparation of Glycidyl Ester Functionalized Organosiloxane Oligomer from Glycidyl Esters Prepared in Example (1B) and Polyhydromethylsiloxane-dimethyl Siloxane Copolymer To a 25 ml toluene solution containing 34 g (0.13 mole) glycidyl ester from (B) above and 0.18 g of 5% $H_2PtCl_6$ in t-amyl alcohol is added a 25 ml toluene solution of 50 g hydromethylsiloxane-dimethylsiloxane copolymer terminated with trimethylsiloxyl groups (30% hydromethylsiloxyl content: M.W.=2050; Si-H equivalent: 60g/per —$CH_3SiH$-0-. Therefore, 50g copolymer containing 0.25 Si-H equivalent) at 70° C. for 10 minutes and heated at 75° C. to 80° C. for 6 hours. A 10 ml toluene solution containing 0.1 g of 5% H2PtCl6 in t-amyl alcohol and 17.7g norborylene (0.22 mole) is then added at 50° C. and heated at 60° C. for another 7 hours. The mixture is dissolved in 100 ml methyl ethyl ketone, and the solution is washed succesively four times with 50 ml portions of $H_2O$. The organic layer is collected and 92 g of viscous liquid (5.0 equiv. glycidyl ester per mole of organosiloxane copolymer, based upon charge and conversion) is obtained after stripping off the solvent and excessive norborlyene at 120° C. to 140° C./<5 mm Hg. The organosiloxane oligomer with glycidyl ester functional groups has an epoxide content of 5.3% (EEW=811.32) and the structure is confirmed by IR and 1H NMR spectra: The Si—H bond absorption at 2100 $cm^{-1}$ and unsaturated double bond at allyl substituent at 1650 $cm^{-1}$ to 1670 $cm^{-1}$ in IR (neat) disappears; In 1H NMR, a strong resonance peak at 0.2ppm to 0.8 ppm for methylsilyl group (Si—$CH_3$ and Si—$CH_2$) appears, while unsaturated allylic double bond at 5 ppm to 6.2 ppm (m, $CH_2$=CH—$CH_2$—) disappears.

(D) Preparation of Glycidyl Ester Functionalized Cyclosiloxane Oligomer from Glycidyl Ester (Example 1B) and 1,3,5,7-tetramethylhydrooctacyclotetrasiloxane To a 20 ml toluene solution containing 42 g (0.16 mole) glycidyl ester from (B) above and 0.15 g of 5% $H_2PtCl_6$ in t-amyl alcohol is added a 10 ml toluene solution of 10 g of 1,3,5,7-tetramethyl cyclotetrasiloxane (M.W.=240.51) at 65° C. to 70° C. in 10 minutes and kept at this temperature for another 6 hours. The mixture is dissolved in 100 ml methyl ethyl ketone, and the solution is washed successively four times with 50 ml portions of $H_2O$. The organic layer is collected and 40 g of viscous liquid (4.0 equiv. glycidyl ester per mole of cyclic organosiloxane, based upon charge and conversion) is obtained after stripping off the solvent at 120° C. to 140° C./<5 mm Hg. The structure is confirmed by IR and 1H NMR spectra. The cyclic organosiloxane with glycidyl ester functional groups has an epoxide content of 10.6% (EEW=405.7) and the structure is confirmed by IR and 1H NMR spectra. The Si—H absorption at 2100 $cm^{-1}$ and unsaturated double bond at allyl substituent at 1650 $cm^{-1}$ to 1670 $cm^{-1}$ in IR(neat) disappeared; In 1H NMR, a strong resonance peak at 0.2 to 0.8 ppm for methylsilyl group (Si—$CH_3$ and Si—$CH_2$) appears, while unsaturated allylic double bond at 5-6.2ppm ($CH_2$=CH—$CH_2$—) disappears.

(E) Preparation of Glycidyl Ester Functionalized Cyclosiloxane Oligomer from Glycidyl Ester (Example 1 -B) and Methylhydrocyclosiloxanes(n=4-8)

To a 30 ml toluene solution containing 72.98(0.27 mole) glycidyl ester from example 1 and 0.15 g of 5% H2PtCl6 in t-amyl alcohol is added a 15 ml toluene solution of 15 g. of methylhydrocyclosiloxanes(n=4-8, e.g=60/ per Si—H, from Hüls, Petrarch co.) at 50°-52° C. in 60 min. and kept at 55° C. for another 6 hrs. The mixture is dissolved in 150 ml methyl ethyl ketone, and the solution is washed successively four times with 50 ml portions of H2O. The organic layer is collected and 81 g of viscous liquid (4.0-6.0 e.g. glycidyl ester/per mole cyclicorganosiloxane , based upon charge and conversion) is obtained after stripping off the solvent at 10°-110° C./<5 mmHg. The cycloorganosiloxane with glycidyl ester functional groups has epoxide content 11.74%(EEW=366) and the structure is confirmed by IR and 1H NMR spectra: The Si bond absorption at 2100-2200 $cm^{-1}$ and unsaturated double bond at allyl substituent at 1650-1670 $cm^{-1}$ in IR(neat) disappeared; In 1H NMR, a strong resonance peak at 0.2-0.8ppm for methylsilyl group (m, Si—CH3 and Si—CH2) appeared, while unsaturated allylic double bond at 5-6.2ppm (m, CH2=CH—CH2—) disappeared.

(F) Preparation of Glycidyl Ester Functionalized Organosiloxane from Glycidy Ester (Example 1-b) and 1,1,3,3-tetramethyldisiloxane To a 30 ml toluene solution containing 54 g (0.2 mole) allyl glycidyl hexahydrophthalate from(1-B) and 0.1g of 5% H2PtCl6 in t-amyl alcohol is added a 20 ml toluene solution of 14.9g of 1,1,3,3-tetramethyldisiloxane(0.1 mole) at 52° C. in 75 min. After completion of additon, the mixture is reacted at 52° C. for another 7 hrs. The mixture is then dissolved in 150 ml methyl ethyl ketone, and the solution is washed successively four times with 50 ml portion of H2O/each. The organic layer is collected and 55 g of product is obtained after stripping off the solvent at 90° C./5 mmHg. The adduct has epoxide content 11.96%(EEW=360) and viscosity 230 cps/40° C. The structure is confirmed by IR and 1H NMR spectra. The Si—H absorption band at 2100 cm$^{-1}$ and unsaturated double bond at allyl substituent at 1650 cm$^{-1}$ in IR(neat) disappeared; In 1H NMR, a strong resonance peak at 0.2–0.5ppm for methylsilyl group(Si—CH3 and Si—CH2) appears, while unsaturated allylic double bond at 5–6.2ppm disappeared.

(G) The Preparation of Glycidyl Ester Functionalized Organosiloxane form Allylglycidyl Ester Hexahydrophthlate of 1B and 1-methyl-1,1,1-tri-(dimethylsiloxyl)-silane To a 25 ml toluene solution containing 34.6g of allylglycidyl hexahydrophthalate(0.12 mole) from 1B and 0.1 g of 5% H2PtCl6 in t-amyl alcohol is added a 15 ml toluene solution of 10.75 g 1-methyl-1,1,1-tri(dimethylsiloxyl) silane(0.04 mole) at 50° C. for 30 min. slightly exothermic is observed. After completion of addition, the mixture is reacted at 55° C. for another 3 hrs, until IR spectrum showed all Si—H absorption band at 2100 cm$^{-1}$ disappeared. The mixture is then dissolved in 150 ml ethylmethylketone and the solution is washed successively with water for four times(50 ml/each). The organic layer is separated and 41 g of adduct is obtained after stripping off the solvent at 120°–130° C./5 mmHg. The glycidyl ester -siloxane adduct has epoxide content 11.70% with EEW 367, viscosity 250 cps/40° C.

(H) Preparation of Glycidyl Ester Functionalized Organosiloxane Oligomer from Glycidyl Ester(Example 1-B) and Polyhydromethylsiloxanedimethylsiloxane Copolymer To a 40 ml toluene solution containing 42.69 g (0.16 mole) glycidyl ester from example 1 and 0.1 g of 5% H2PtCl6 in t-amyl alcohol is added a 20 ml toluene solution of 50 g of polymethylhydrosiloxanesdimethylsiloxane copolymer (18% hydromethyl siloxane content; M.W.=2250; Si—H equivalent: 60g/per Si—H, from Huls Co.) at 50°–52° C. in 120 min., and kept at 55° C. for another 1.5 hrs. The mixture is dissolved in 150 ml methyl ethyl ketone, and the solution is washed successively four times with 50 ml portions of H2O. The organic layer is collected and 90 g of viscous liquid is obtained after stripping off the solvent at 100°–110° C./5 mm Hg. The organosiloxane with glycidyl ester functional groups has an epoxide content of 7.18% (EEW=599) and the structure is confirmed by IR and 1H NMR spectra: The Si bond absorption at 2100–2200 cm$^{-1}$ and unsaturated double bond at allyl substituent at 1650–1670 cm$^{-1}$ in IR(neat) disappears: In 1H NMR, a strong resonance peak at 0.2–0.8ppm for methylsilyl group (m, Si—CH3 and Si—CH2) appeared, while unsaturated allylic double bond at 5–6.2ppm (m, CH2=CH—CH2—) disappears.

EXAMPLE 2

(A) Preparation of the Unsaturated Mono-ester Acid Adduct from Hexahydrophthalic Anhydride and Norborene Methanol A 500 ml four-necked, round bottom flask equipped with a cooling condenser, mechanical stirrer, thermometer with temperature controller and nitrogen source is placed on a heating mantle. Hexahydrophthalic anhydride (HHPA, 0.75 mole, 115.6 g, >95% purity and norborenemethanol (0.75 mole, 97 g, >98% purity) are charged into the flask and carefully heated to 65° C. to 70° C. The melted mixture is reacted at 85° C. for 8 hours. The unreacted norborene methanol is further stripped off from the viscous adduct of HHPA-norborenemethano at 130° C./<5 mm Hg. 205 g. of HHPA-norborenemethanol monoester adduct is obtained. IR shows that absorption bands at 1860 cm$^{-1}$ and 1800 cm$^{-1}$ for anhydride carbonyl group are substituted by two strong absorption bands at 1700 cm$^{-1}$ and 1730 cm$^{-1}$, which represents the carbonyl groups both of ester and carboxylic acid, together with a broad carboxylic acid OH absorption peak at 3000 cm$^{-1}$ to 3500 cm$^{-1}$. 1H NMR (CDCl3-TMS) shows the appearance of unsaturated double bond of norborene at 5.7 ppm to 6.3 ppm together with the —OCH2-multiple peaks at 3.8 ppm to 4.2 ppm (diastereotropic position) for norborenemethanol mono-ester. The carboxilic absorption peak of the adduct is at 10 ppm to 11 ppm which disappears later after epoxidation.

(B) Preparation of the Glycidyl Ester of the Unsaturated Mono-ester Acid Adduct from Hexahydrophthalic Anhydride and Norborene Methanol A 500 ml four-necked round bottom flask equipped with a cooling condenser, mechanical stirrer, thermometer with temperature controller and addition funnel is placed on a heating mantle. 64 g (0.23 mole) of the mono-ester acid adduct from HHPA and norborenemethanol prepared in (A) above, epichlorohydrin 171 g, 1.84 mole), and tetrabutyl ammonium chloride (0.50g, 0.002 mole) are charged into the flask. The mixture is carefully heated to 65° C. and kept at 65° C. for another 2.5 hours. IR spectra of the reaction mixture shows all carboxilic groups of mono-ester acid adduct from HHPA and norborenemethanol reacts with epichlorohydrin to form chlorohydrin ester. The reaction mixture is then cooled to 45° C. 33.12 g of 50% NaOH aqueous solution (0.42 mole) is added at this temperature over a period of about 30 minutes, and occasionally cooling is necessary in order to prevent exothermic reaction. After the completion of addition, the reaction is maintained at 45° C. for another 4 hours. After filtrations, to the solution is added 250 ml to 300 ml methyl ethyl ketone (MEK) and successively neutralized with dry ice followed by washing with water (100 ml each for five times). The unreacted epichlorohydrin and MEK is then stripped off under vacuum (<5mmHg) at 100° C. to13° C. 68 g. of glycidyl ester of HHPA-norborenemethanol mono-ester acid adduct is obtained having an epoxide content of 12.8% (EEW =335.9). Theoretical epoxide content is 12.8% (EEW =335.9).

(C) Preparation of Hydrosilylation Adduct of Glycidyl Ester (Example 2B) and 1,1,3,3-tetramethyldisiloxane To a 20 ml toluene solution containing 53.5g (0.16 mole) glycidyl ester prepared in (B) above and 0.15g of a 5% solution of H2PtCl6 in t-amyl alcohol is added a 20 ml toluene solution containing 10.8 g (0.078 mole) tetramethyldisiloxane at 65° C. The addition is complete in 15 minutes no exothermeric reaction is observed. The mixture is heated at 65° C. to 70° C. for another 9 hours. Toluene, 100 ml, is added into the reactor, after washing successively with water (50 ml each for 4 times), 55 g of the viscous product: 1,3-bis-(5-norborenyl-2-methyl-(2'- glycidyl carboxy)-1'-cyclohexanecarboxylate)-1,1,3,3-tetramethyldisiloxane is obtained after stripping off solvent at 1205° C./<5 mm Hg. Epoxide content=11.56% (EEW=371.9). The structure of the hydrosilylation adduct is confirmed by 1H NMR and IR analysis: The Si-H bond absorption at 2100 cm$^{-1}$ in IR (neat) disappears; In 1H NMR, a strong resonance peak at 0.2 ppm to 0.8 ppm for methyl silyl group (Si—CH$_3$ and Si—CH$_2$) appears, while unsaturated norborene double bond at 5.8 ppm to 6.2 ppm (—CH=CH—) disappears.

EXAMPLE 3

Reactivity And Cured Product Properties Of Example 1

The reactivity of the mixture of uncured glycidyl ester functionalized siloxane (Examples 1-C, 1-D, 1-E, and 1-F) with hexahydrophthalic anhydride/catalyst is measured by differential scanning calorimetry(DSC) method using a Du Pont series 2100 thermal analysis system with DSC model no. 912. The results are given in the following Table I.

TABLE I

| Resin | Curing Agent | Catalyst | DSC Exotherm Temp. Init. (°C.) | Max. (°C.) |
|---|---|---|---|---|
| 1C (2.43 G) | HHPA$^a$ (0.44 g) | 2-MI$^b$ (0.01 g) | 121 | 161 |
| 1D (2.0 g) | HHPA (0.73 g) | 2-MI$^b$ (0.01 g) | 115 | 150 |
| 1E (1.95 g) | HHPA (0.73 g) | 2-MI$^b$ (0.01 g) | 121 | 150 |
| 1E (1.95 g) | HHPA (0.73 g) | A-1$^c$ (0.01 g) | 124 | 157 |
| 1F (2.16 g) | HHPA (0.73 g) | 2-MI$^b$ (0.01 g) | 115 | 144 |
| 1F (2.16 g) | HHPA (0.73 g) | A-1 (0.01 g) | 125 | 158 |
| CY-184$^{d*}$ (0.77 g) | HHPA (0.73 g) | 2-MI$^b$ (0.01 g) | 122 | 143 |

*Not an example of the present invention.
$^a$HHPA is hexahydrophthalic anhydride.
$^b$2-MI is 2-methylimidzole.
$^c$A-1 is a 70 percent methanol solution of ethyl triphenyl phosphonium acetatate.acetic acid complex.
$^d$CY-184 is diglycidyl ester of hexahydrophthalic acid (EEW 184) from Ciba-Geigy.

EXAMPLE 4

Coating compositions (Formulations 4-A to 4-D) containing organosiloxane-glycidyl esters of the invention is formulated using a phosphonium catalyst and anhydride curing agent.

The anhydride curing agent is cyclohexane-1,2dicarboxylic anhydride. The curing agent is used in an amount corresponding to 95 equivalent percent of the epoxide equivalent. The catalyst is 4.5% weight of anhydride used. The curing catalyst is 70% methanol solution of ethyltriphenylphosponium acetate.acetic acid complex (ETPPA.HAc) and is employed in an amount of 4.5 weight percent of the amount of anhydride employed.

A comparative coating composition (Formulation 4-E) using diglycidyl ester of hexahydrophthalate (DGEHHPA, epoxide content=27.04%, EEW=159) instead of organosiloxane-glycidyl esters is also formulated using the same phosphonium catalyst and anhydride curing agent.

The compositions (formulations 4A-E) are reduced to a spray viscosity of 30-32 seconds measured with a No.2 Zahn cup by adding butyl acetate. The coating compositions are sprayed onto a steel panel and cured at 250° F. (121.1° C.) for 30 minutes and at 325° F. (162.8° C.) for another 30 minutes to form a 2 mil (0.0508 mm) coating thickness. The coatings containing the organosiloxane moiety gave excellent flexibility compared to the coating containing only the diglycidyl ester of hexahydrophthalate (DGEHHPA). The results are given in the following Table II.

TABLE II

| | Formulation | | | | |
|---|---|---|---|---|---|
| | A | B | C | D | E* |
| Glycidyl Ester Type/grams | Ex 1-E/15 | Ex 1-H/15 | Ex 1-E/13.5 Ex 1-H/3.5 | Ex 1-H/3.5 DGEHHPA/13.5 | DGEHHPA/15 |
| Curing Agent (HHPA), grams | 6.53 | 3.68 | 6.88 | 13.47 | 13.82 |
| Catalyst, ETPPA.HAc grams | 0.30 | 0.16 | 0.30 | 0.61 | 0.60 |
| Solvents, grams | | | | | |
| n-butyl acetate | 3 | 3 | 3 | 3 | 3 |
| Xylene | 1 | 1 | 1 | 1 | 1 |
| Aromatic 100 | 1 | 1 | 1 | 1 | 1 |
| Properties | | | | | |
| Forward Impact | | | | | |
| In-lb | 60–80 | >100 | 100–120 | 50 | 20–40 |
| Kg-cm | 69–92 | >115 | 115–138 | 58 | 23–46 |

*Not an example of the present invention.

What is claimed is:

1. A compound containing at least one glycidyl ester group and at least one organosiloxane moiety

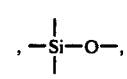

per molecule represented by the following general formulas V, VI, VII, or VIII

Formula V

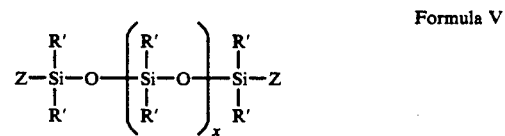

Formula VI

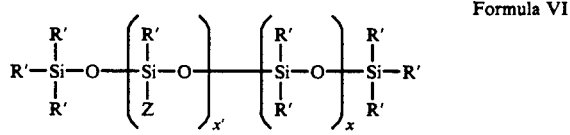

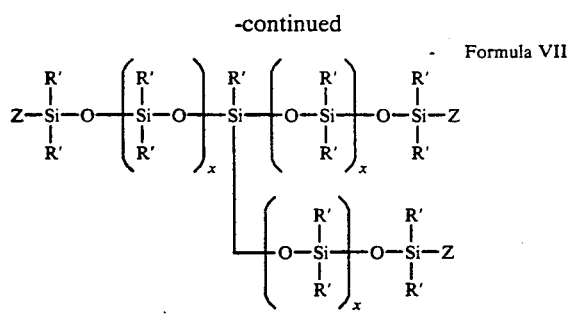

Formula VII

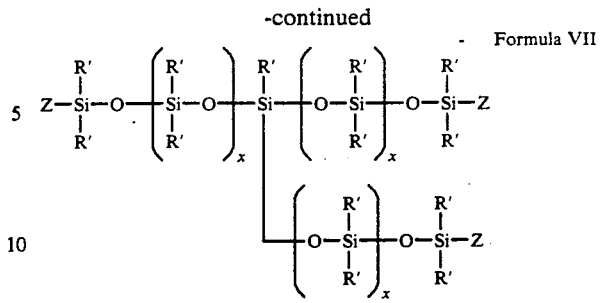

Formula VII

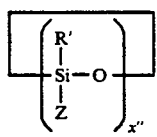

Formula VIII

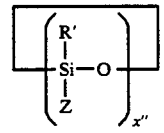

Formula VIII wherein each R' is independently a hydrocarbyl group or hydrocarbyl group substituted with N or F containing groups, said hydrocarbyl group having from 1 to about 20 carbon atoms; each Z is an aliphatic or cycloaliphatic group containing a glycidyl ester moiety represented by the general formula —X—R$^5$—(COOR$^4$)$_{n'}$, with the proviso that the Z group is attached directly to a silicon atom; R$^5$ is an aliphatic or cycloalilphatic or aromatic group or a S, N or P containing heterocyclic group having from 1 to about 50 carbon atoms; R$^4$ is a glycidyl group or lower alkyl (C$_{1-4}$) substituted glycidyl group; n' has a value from 1 to about 20; each X is independently a divalent aliphatic or a divalent cycloaliphatic group having from 2 to about 30 carbon atoms; each x independently has a value from zero to about 500; each x' independently has a value from 2 to about 500; x" has a value from 3 to about 50; and the sum of x and x' is from about 2 to about 1000.

2. A process for preparing compounds containing at least one glycidyl ester group and at least one siloxane moiety

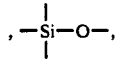

per molecule represented by the following formulas V, VI, VII or VIII

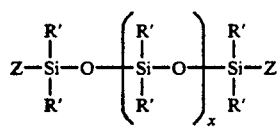

Formula V

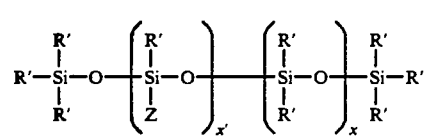

Formula VI wherein R' is independently a hydrocarbyl group or hydrocarbyl group substituted with N or F containing groups, said hydrocarbyl group having from 1 to about 20 carbon atoms; each Z is an aliphatic or cycloaliphatic group containing a glycidyl ester moiety represented by the general formula —X—R$^5$—(COOR$^4$)n', with the proviso that the Z group is attached directly to a silicon atom; R$^5$ is an aliphatic or cycloalilphatic or aromatic group or a S, N or P containing heterocyclic group having from 1 to about 50 carbon atoms; R$^4$ is a glycidyl group or lower alkyl (C$_{1-4}$) substituted glycidyl group; n' has a value from 1 to about 20; each X is independently a divalent aliphatic or a divalent cycloaliphatic group or a divalent alkoxy or a divalent cycloalkoxy group having from 2 to about 30 carbon atoms; each x independently has a value from zero to about 500; each x' independently has a value from 2 to about 500; x" has a value from 3 to about 50; and the sum of x and x' is from about 2 to about 1000 which process comprises reacting (1) at least one compound containing at least one glycidyl ester group per molecule and at least one unsaturated aliphatic or cycloaliphatic group per molecule; with (2) a compound containing at least one hydrosiloxane moiety per molecule represented by the following formulas I, II, III or IV

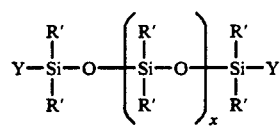

Formula I

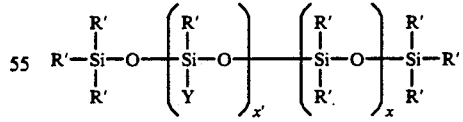

Formula II

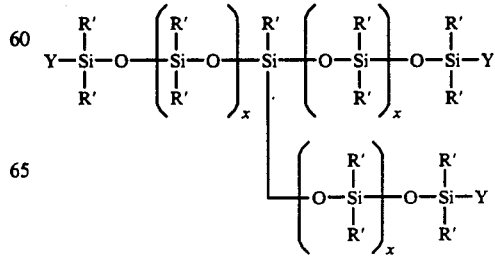

Formula III

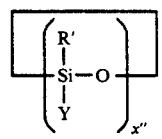

Formula IV wherein R',x,x' and x" are as defined above and Y is hydrogen.

3. A process of claim 2 wherein the reaction is conducted at a temperature of from about 0° C. to about 150° C. and the components are employed in amounts which provide an equivalent ratio of hydrosiloxane-containing compound to unsaturated glycidyl ester-containing compound of from about 0.25:1 to about 25:1; and the reaction is conducted in the presence of a catalytic amount of a catalyst.

4. A process of claim 2 wherein component (1) is a compound or a mixture of compounds represented by the following general formula

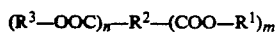

wherein $R^1$ is a saturated or unsaturated aliphatic, saturated or unsaturated cycloaliphatic, aromatic, or sulfur, nitrogen or phosphorus containing heterocyclic, saturated or unsaturated cycloaliphatic or aromatic group; $R^2$ is a saturated or unsaturated aliphatic or saturated or unsaturated cycloaliphatic, or sulfur, nitrogen or phosphorus containing heterocyclic saturated or unsaturated cycloaliphatic group; $R^3$ is clycidyl group or lower alkyl ($C_1$-$C_4$) substituted glycidyl group; and each n and m independently has a value from about 1 to about 20; and with the proviso that there is at least one unsaturated moiety in each molecule undergoing hydrosilylation and when $R^2$ contains an unsaturated moiety, $R^1$ can be a glycidyl group.

5. A process of claim 4 wherein the reacting is conducted at a temperature of from about 30° C. to about 120° C.

6. A process of claim 4 wherein the reacting is conducted at a temperature of from about 40° C. to about 120° C. and component (1) is allyl glycidyl hexahydrophthalate, crotyl glycidyl hexahydrophthalate, 3-butenyl glycidyl hexanydrophthalate, norborene methyl glycidyl hexahydrophthalate, diglycidyl bicyclo-(2.2.1)-hepta-5-ene-2,3-dicrboxylate, or diglycidyl tetrahydrophthalate; and component (2) is 1,1,3,3-tetramethyldisiloxane; 1,1,3,3,4,4-hexamethyltrisiloxane; 1,1,3,3,5,5,7,7-octamethyltetrasiloxane; 1,3-diphenyl-1,3-dimethyldisoloxane; 1,1,3,3-tetraisopropyldisiloxane; 1,3-diphenyl-1,1,3,3-tetrakis-(dimethylsiloxyl)-disiloxane; 1,3,5,7-tetramethylcyclotetrasiloxane; 1,3,5,7,9-pentamethylcyclopentasiloxane; 1,3,5,7,9,11-hexamethylcyclohexasiloxane; 1,1,3,3-tetrakis-(trimethylsiloxyl)-disiloxane; polymethylhydrosiloxane weight average M.W.=300–50,000; methylhydrodimethylsiloxane copolymer weight average M.W.=120–100,000; dimethylterminated-methylhydro-phenylmethylsiloxane copolymer weight average M.W.=120–100,000; or a combination of any two or more of such compounds.

7. A curable composition comprising (A) a compound containing at least one glycidyl ester group and at least one organosiloxane moiety

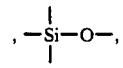

per molecule represented by the following formulas V, VI, VII or VIII

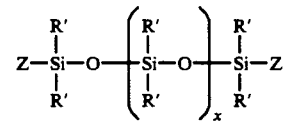

Formula V

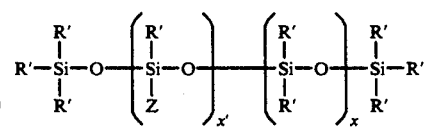

Formula VI

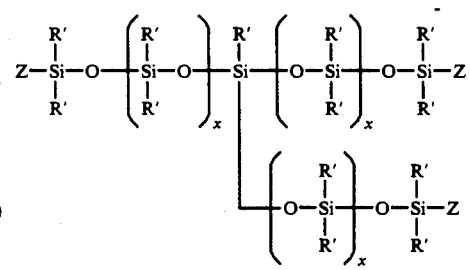

Formula VII

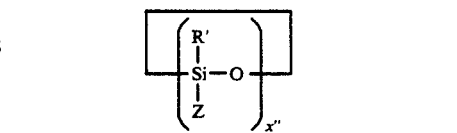

Formula VIII wherein each R' is independently a hydrocarbyl group or hydrocarbyl group substituted with N or F containing groups, said hydrocarbyl group having from 1 to about 20 carbon atoms; each Z is an aliphatic or cycloaliphatic group containing a glycidyl ester moiety represented by the general formula —X—$R^5$—(COOR$^4$)n', with the proviso that the Z group is attached directly to a silicon atom; $R^5$ is an aliphatic or cycloalilphatic or aromatic group or a S, N or P containing heterocyclic group having from 1 to about 50 carbon atoms; $R^4$ is a glycidyl group or lower alkyl ($C_{1-4}$) substituted glycidyl group; n' has a value from 1 to about 20; each X is independently a divalent aliphatic or a divalent cycloaliphatic group or a divalent alkoxy or a divalent cycloalkoxy group having from 2 to about 30 carbon atoms; each x independently has a value from zero to about 500; each X' independently has a value from 2 to about 500; x" has a value from 3 to about 50; and the sum of x and x' is from about 2 to about 1000; and (B) a curing quantity of a curing agent for component (A).

8. A product or article resulting from curing a curable composition of claim 7.

9. A coating composition comprising an organic carrier, and a curable composition of claim 7; said carrier being employed in an amount to provide the coating composition with a suitable application viscosity.

10. An article coated with the coating composition of claim 9 which coating has subsequently been cured.

* * * * *

UNITED STATES PATENT AND TRADEMARK OFFICE
CERTIFICATE OF CORRECTION

PATENT NO. : 5,188,903  Page 1 of 2
DATED : February 23, 1993
INVENTOR(S) : Zeng, K. Liao, James L. Bertram It is certified that error appears in the above-indentified patent and that said Letters Patent is hereby corrected as shown below:

COLUMN 21,

In Claim 4, line 33, reads as:

"cycloaliphatic group; $R^3$ is clycidyl group or lower"

shoud read as:

-- cycloaliphatic group; $R^3$ is a glycidyl group or lower--

In Claim 6, line 51, reads as:

"ramethyldisiloxane; 1,1,3,3,4,4-hexamethyltrisiloxane;"

should read as:

--ramethyldisiloxane; 1,1,3,3,5,5-hexamethyltrisiloxane;--

UNITED STATES PATENT AND TRADEMARK OFFICE
CERTIFICATE OF CORRECTION

PATENT NO. : 5,188,903
DATED : February 23, 1993
INVENTOR(S) : Zeng K. Liao, James L. Bertram It is certified that error appears in the above-indentified patent and that said Letters Patent is hereby corrected as shown below:

Column 21,

In Claim 6, line 53,    reads as:

"1,3-dimethyldisoloxane; 1,1,3,3-tetraisopropyldisilox-"

should read as:

--1,3-dimethyldisiloxane; 1,1,3,3-tetraisopropyldisilox- --

Signed and Sealed this

Twenty-second Day of March, 1994

Attest:

BRUCE LEHMAN

*Attesting Officer*    *Commissioner of Patents and Trademarks*